United States Patent [19]
Sano et al.

[11] Patent Number: 5,120,507
[45] Date of Patent: Jun. 9, 1992

[54] REFLECTION PLATE FOR A BIOCHEMICAL MEASURING INSTRUMENT

[75] Inventors: Yoshihiko Sano; Shigeru Makita, both of Kyoto, Japan; Maury Zivitz; George H. Sierra, both of Indianapolis, Ind.

[73] Assignees: Omron Tateisi Electronics Co., Kyoto, Japan; Boehringer Mannheim Corporation, Indianapolis, Ind.

[21] Appl. No.: 272,365

[22] Filed: Nov. 17, 1988

[30] Foreign Application Priority Data

Nov. 24, 1987 [JP] Japan ................. 62-178537

[51] Int. Cl.$^5$ ............................................. G01N 21/27
[52] U.S. Cl. ..................... 422/82.05; 356/238; 356/408; 422/68.1
[58] Field of Search ............. 422/68.1, 82.05; 350/110; 356/238, 408

[56] References Cited

U.S. PATENT DOCUMENTS

| | | |
|---|---|---|
| 4,035,085 | 7/1977 | Seiner. |
| 4,509,859 | 4/1985 | Markart et al. ............. 422/82.05 |
| 4,780,283 | 10/1988 | Meinecke et al. ............ 422/82.05 |

*Primary Examiner*—Jill A. Johnston
*Attorney, Agent, or Firm*—Fish & Richardson

[57] ABSTRACT

A reflection plate for a biochemical measuring instrument which is adapted to evaluate a biochemical value by obtaining a reflective property of a reflection surface of the reference reflection plate, obtaining a reflective property of test paper impregnated with biochemical sample and mounted on a test stick, and comparing the two reflective properties, wherein: the reflection surface of the reference reflection plate is depressed from the periphery thereof. Thereby, even though the test stick is required to be placed adjacent to the reflection surface to achieve a uniformity the optical arrangement in obtaining the two reflective properties, the contamination of the reflection surface from the sample can be prevented. Preferably, the reference reflection plate itself may be provided with a depression to defined the reflection surface at the bottom of this depression.

3 Claims, 5 Drawing Sheets

REFLECTION PLATE FOR A BIOCHEMICAL MEASURING INSTRUMENT

TECHNICAL FIELD

The present invention relates to an improved reference reflection plate for a biochemical measuring instrument, such as a urine sugar meter, a blood sugar meter or the like, which provides a reflection surface of a known or reference reflective property. A measurement of the reflective property of the reference reflection surface produces a blank value which serves as a reference value for actual measurements of the reflective properties of various samples. In particular, the present invention is related to a reference reflection plate which is free from deterioration due to deposition of samples on the reflection surface.

BACKGROUND OF THE INVENTION

Conventionally, various biochemical measurements have been performed by using test paper pieces impregnated with various reagents. These test paper pieces are wetted with biochemical substances, such as urine, blood, and so on, and the color changes in these test paper pieces resulting from various color reactions are evaluated visually or by photoelectric devices.

FIG. 6 is an enlarged view of an essential part of such a conventional photoelectric biochemical measuring instrument. This biochemical measuring instrument comprises a meter main body 72 which is internally incorporated with a reflection sensor 71 consisting of a light emitting element and a light receiving element, and a test paper cover 74 which is urged by a spring 73 towards the meter main body 72, defining an insertion passage 77 for receiving a test stick 76 consisting of a synthetic resin strip between the meter main body 72 and the test paper cover 74. On the test stick 76 is mounted a piece of test paper 75 impregnated with a suitable reagent. The reflection sensor 71, which is electrically connected to an electronic circuit unit, faces an opening 78 which is provided in the meter main body 72 for conducting light from the reflection sensor 71 to the test paper 75 and then back to the reflection sensor 71. A reference reflection plate 79 for measuring a blank value is fixedly attached to the test paper cover 74 opposite to the opening 78.

To perform a biochemical measurement such as a measurement of a urine sugar value, light is projected from the light emitting element of the reflection sensor 71 onto the reference reflection plate 79 as shown in FIG. 7, and the light reflected from the reference reflection plate 79 is received by the light receiving element of the reflection sensor 71 as a reading of a blank value or a reference value. Thereafter, sample, in this case urine, is impregnated in the test paper 75 of the test stick 76, which is then left as it is for a certain time interval required for the required color reaction. Then, the test stick 76 is inserted into the test stick insertion passage 77 which is opened up by sliding back the test paper cover 74 against the force of the spring 73. In this state, the face of the test paper 75 opposes the reflection sensor 71 via the opening 78, and the test stick 76 is pressed between the peripheral part of the opening 78 and the reference reflection plate 79 as shown in FIG. 8.

Here, light is projected from the light emitting element of the reflection sensor 71 onto the surface of the test paper 75, and the light reflected therefrom is captured by the light receiving element of the reflection sensor 71 for evaluating the urine sugar value from the intensity of the captured colored light by comparing the intensity of the captured light with the blank value and displaying it on a display unit.

However, this conventional reflection plate is generally planar, and is, in particular, provided with a planar reflection surface. Therefore, the reflection surface of the reference reflection plate will contact the reverse surface of the test stick which faces away from the test paper. Therefore, when an excessive amount of sample, which may consist of urine, blood or the like, is impregnated in the test paper, the sample could be deposited from the test stick onto the reflection surface of the reference reflection plate. Such a deposition prevents an accurate measurement of the blank value by altering the reflection property of the reflection surface, and substantially impairs the accuracy of the biochemical measurement.

Furthermore, since the test paper cover is required to be slid back before a test stick is inserted into the biochemical measuring instrument, handling is not very favorable.

Copending U.S. patent application Ser. No. 072,817 filed Jul. 13, 1987, discloses a photoelectric biochemical measuring instrument, and the disclosure of this prior application is hereby incorporated in the present application by reference.

BRIEF SUMMARY OF THE INVENTION

A primary object of the present invention is to eliminate such problems and to provide a reference reflection plate for measuring a blank value in a photoelectric biochemical measuring instrument in which deposition of sample onto the reflection surface of the reference reflection plate is prevented so as to ensure an accurate measurement of a blank value every time.

A second object of the present invention is to provide a reference reflection plate for a photoelectric biochemical measuring instrument which is durable by being free from contamination even when it is used for a large number of measurements.

A third object of the present invention is to provide a reference reflection plate for a photoelectric biochemical measuring instrument which is easy to use.

These and other objects of the present invention can be accomplished by providing a reference reflection plate for a biochemical measuring instrument which is adapted to evaluate a biochemical value by obtaining a reflective property of a reflection surface of the reference reflection plate, obtaining a reflective property of test paper impregnated with biochemical sample and mounted on a test stick, and comparing the two reflective properties, wherein: the reflection surface of the reference reflection plate is depressed from the periphery thereof.

The reflection surface may be depressed from its periphery by providing a depression in a central part of the reference reflection plate itself, and the bottom surface of the depression serves as the reflection surface. Alternatively, a frame may be placed between the test stick and the reference reflection place which, in this case, may be provided with an entirely planar surface. In any case, since the reflection surface is depressed from the periphery thereof, it would not come into contact with the test stick which is required to be placed adjacent to the reflection surface to achieve a uniformity in the optical arrangement in obtaining the two reflection properties, and is therefore protected from being contaminated with the sample. Therefore, the light emitted from the light emitting element of the reflection sensor is projected upon this depressed reflection surface, and the light reflected therefrom is captured by the light receiving element for measuring a blank value. When a test stick carrying a piece of test paper impregnated with sample (urine or blood) is inserted in the insertion passage, the reverse surface of the test stick contacts the reference reflection plate in the same manner as in the case of a conventional reference reflection plate. However, since the reflection surface of the reference reflection plate is depressed from the plane of the other part of the surface of the reference reflection plate, the reverse surface of the test stick contacts only the outer periphery of the reflection surface, defining a gap corresponding to the depth of the depression between the reflection surface and the test stick, and the sample is positively prevented from contaminating the reflection surface as opposed to conventional reference reflection plates. Thus, accurate measurement of a blank value is always possible, and the measurement accuracy can be improved.

According to a certain feature of the present invention, the reflection plate is carried by a moveable head which carries the reflection plate in a free end thereof and is biased by spring means so as to press upon the reverse surface of a test stick when it is inserted into the insertion passage, the head being provided with a guide surface which guides the test stick into the insertion passage against the biasing force of the spring means. Thus, the user of the biochemical measuring instrument may simply insert a test stick into the insertion passage against the biasing force of the spring means. And the moveable head is displaced by the test stick, which is guided by the guide surface, against the spring force of the spring means, and the test stick is properly received in the insertion passage.

BRIEF DESCRIPTION OF THE DRAWINGS

Now the present invention is described in the following with reference to the appended drawings, in which.

DETAILED DESCRIPTION OF THE PREFERRED EMBODIMENT

Figure 1:
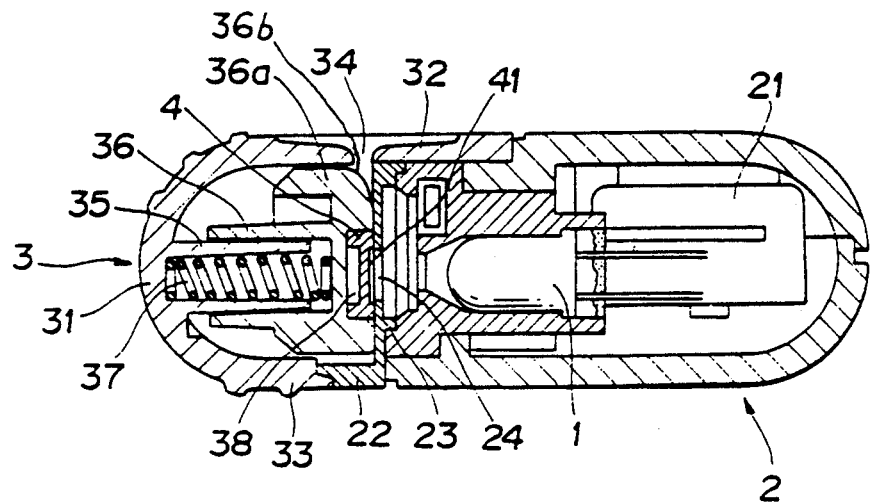
FIG. 1 is a sectional view showing a biochemical measuring instrument equipped with a reference reflection plate for measuring a blank value according to the present invention.

FIG. 1 is a sectional view showing a biochemical measuring instrument equipped with a reference reflection plate for measuring a blank value according to the present invention.

This biochemical measuring instrument comprises a meter main body 2 incorporated with a reflection sensor consisting of a light emitting element and a light receiving element, and a test paper cover 3 which can be snap fit onto the meter main body 2 as described hereinafter. The meter main body 2 is incorporated with an electronic circuit unit 21 which is electrically connected to the reflection sensor 1, and is provided with a planar stick holder plate 23 which is fixedly secured to the open end of the meter main body 2 and provided with a receiver plate 22 at its lower end. An opening 24 communicating with the reflection sensor 1 is provided in the central part of the stick holder plate 23.

Figure 2:
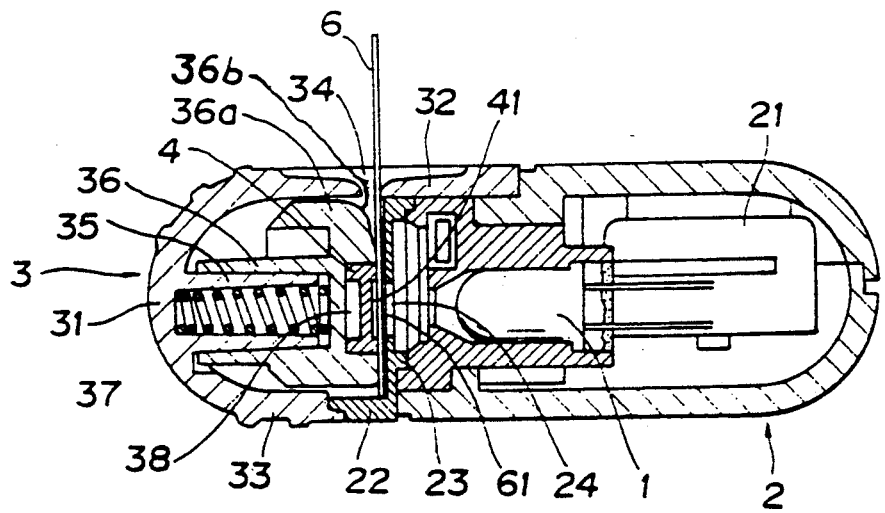
FIG. 2 is a sectional view showing the manner of evaluating the color reaction of test paper by using the biochemical measuring instrument of the present embodiment.

The test paper cover 3 has a C-shaped cross section by being provided with a central curved portion 31 and an upper surface plate 32 and a lower surface plate 33 extending from either end portion of the central curved portion 31. The test paper cover 3 is additionally provided with a pair of elastic legs which integrally project from either lateral side of the central curved portion 31 although it is not shown in the drawings. The free ends of these legs are provided with external projections which are also not shown in the drawings but can elastically engaged with corresponding shoulder surfaces defined in the interior of the meter main body 2. Thus, in this way or in any other suitable way, the test paper cover 3 can be snap fitted onto the meter main body 2 by resilient engagement and can also be detached from the meter main body 2 by pulling it away from the meter main body 2 with a sufficient force. The upper surface plate 32 is provided with an opening 34 for receiving a test stick 6 as shown in FIG. 2, and the free ends of the upper and lower surface plates 32 and 33 abut corresponding shoulder surfaces of the meter main body 2 when the test paper cover 3 is snap fitted onto the meter main body 2. Thus, the test paper cover 3 can be attached to and removed from the meter main body 2 as desired.

From the central curved portion 31 of the test paper cover 3 projects a tubular portion 35, in parallel with the upper and lower surface plates 31 and 32, and a tubular stick holder member 36 having an enlarged head 36a is fitted into the tubular portion 35. A compression coil spring 37 is interposed between the bottom surface of the tubular portion 35 and the stick holder member 36 to urge the head 36a of the stick holder member 36 towards the stick holder plate 23. A cavity 38 is provided in the free end of the head 36a of the stick holder member 36 for receiving a reference reflection plate 4 therein. Under normal condition, the free end of the head 36a of the stick holder member 36 is generally in contact with the surface of the stick holder plate 23, and the front surface of the reference reflection plate 4 opposes the opening 24 in the stick holder plate 23.

The primary feature of the present invention is found in the provision of means for preventing the deposition of foreign matters on the reference reflection plate 4.

Figure 3:
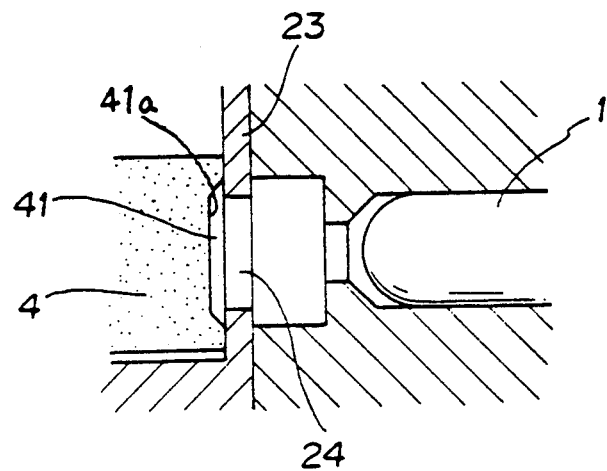
FIG. 3 is an enlarged sectional view of the reference reflection plate.

The means for preventing the deposition of foreign matters is built as an inwardly depressed depression 41 provided in the surface of the planar reference reflection plate 4 facing the reflection sensor 1 via the opening 24 in the stick holder plate 23, to define the reflection surface at the bottom surface 41a of the depression 41 as best shown in FIG. 3. Under normal condition, the part of the surface of the reference reflection plate 4 which is peripheral to the depression 41 contacts the stick holder plate 23, and the light projected from the light emitting element of the reflection sensor 1 projects upon the reflection surface at the bottom surface 41a of the depression 41 through the opening 24.

In actually performing a biochemical measurement using a biochemical measuring instrument equipped with such a reflection plate for measuring a blank value as described above, under normal condition, the head 36a of the stick holder member 36 initially contacts the stick holder plate 23, and the reflection surface at the bottom of the depression 41 opposes the opening 24. A blank value is detected by projecting the light from the light emitting element of the reflection sensor 1 onto the reflection surface at the bottom of the depression 41, and capturing the light reflected therefrom with the light receiving element of the reflection sensor 1. Then, the test paper 61 mounted on the test stick 6 is impregnated with sample, for instance urine, and, after elapsing of a certain time interval required for the color reaction, the test stick 6 is inserted into the opening 34 of the upper surface plate 32. Since the part of the head 36a of the stick holder member 36 adjacent to this opening 34 is rounded to define a guide surface 36b, the inserted test stick 6 pushes the stick holder member 36 away from the stick holder plate 23 against the spring force of the compression coil spring 37, whereby a gap is defined between the head 36a of the stick holder member 36 and the stick holder plate 23 to accommodate the test stick 6 therebetween.

Figure 4:
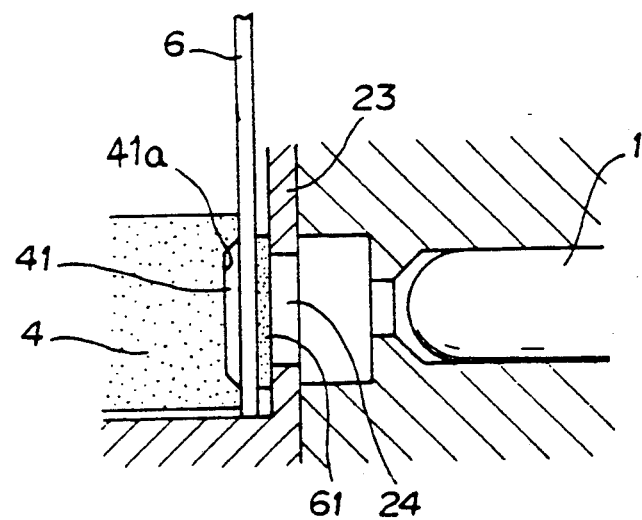
FIG. 4 is a sectional view of an essential part of the relationship between the reference reflection plate and the inserted test stick.

In this state, the test paper 61 opposes the opening 24, and the test stick 6 is fixed against the stick holder plate 23 by the pressure from the stick holder member 36. Further, the peripheral part of the reference reflection plate 4 contacts the reverse surface of the test stick 6. Since the front surface of the reference reflection plate 4 which faces the test stick 6 is provided with the depression 41, a gap corresponding to the depth of the depression 41 is defined between the reference reflection plate 4 and the reverse surface of the test stick 6. In other words, there is no contact between the reflection surface at the bottom of the depression 41 and the test stick 6 itself as best shown in FIG. 4.

Therefore, even when the amount of the sample, for instance urine, impregnated in the test paper 61 happens to be excessive, and the sample has wetted the back of the test stick 6, the contamination of the reflection surface 41 of the reference reflection plate 4 can be prevented and the detection of a proper blank value is possible thereafter, with the result that the measurement accuracy of the measuring instrument can be maintained even after a large number of measurements have been carried out with the same reference reflection plate.

The structures of the test paper cover and the mounting structure for the test paper cover and the reference reflection plate are not limited by those adopted in the above described embodiment since the present invention is characterized by depressing the reflection surface of the reference reflection plate from its periphery.

Figure 5:
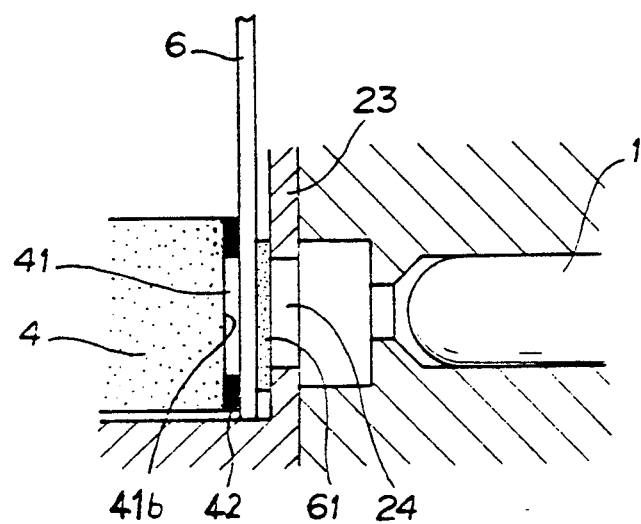
FIG. 5 is a view similar to FIG. 4 showing a modified embodiment of the present invention.
Figure 6:
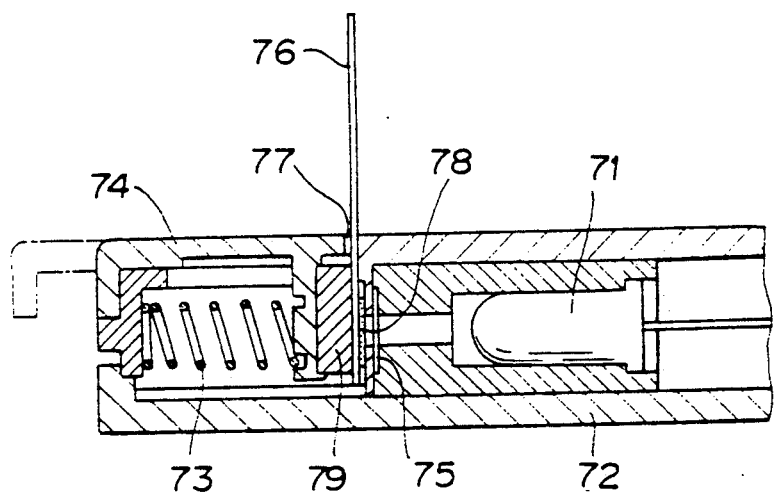
FIG. 6 is a sectional view of an essential part of a biochemical measuring instrument equipped with a conventional reference reflection plate.
Figure 7:
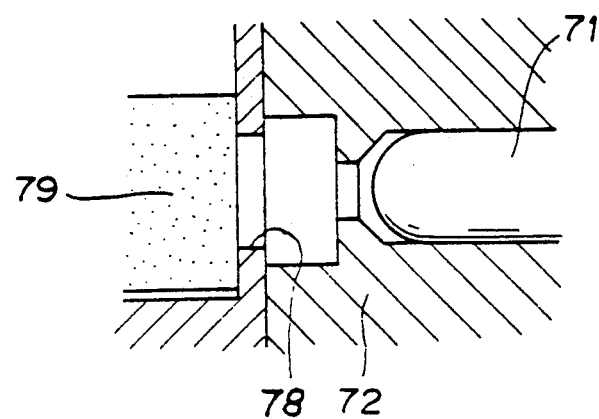
FIG. 7 is an enlarged sectional view of an essential part of the conventional reference reflection plate.
Figure 8:
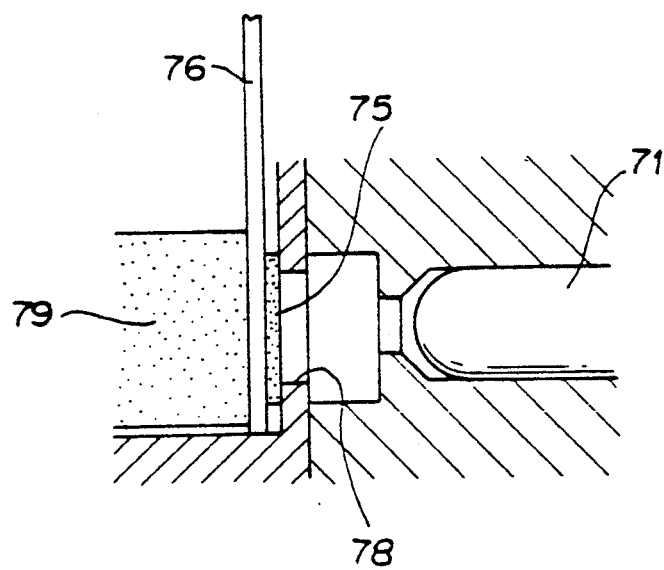
FIG. 8 is an enlarged sectional view of an essential part of the relationship between the conventional reference reflection plate and an inserted test stick.

Alternatively, as shown in FIG. 5, it is possible to provide a frame 42 in front of the reference reflection plate. In this case, the reference reflection plate may be provided with an entirely flat and planar surface 41b.

In either case, since the test paper cover 3 is detachable, the reference reflection plate may be readily replaced either for different applications and for servicing purpose.

Thus, according to the present invention, since a depression is provided in the front surface of the reference reflection plate to permit the use of the bottom surface of the depression as the reflection surface itself, when a test stick is inserted into the insertion passage, no contact occurs between the reverse surface of the test stick and the reflection surface of the reference reflection plate, and the sample impregnated in the test paper would not be deposited onto the reflection surface of the reference reflection surface. Therefore, not only the contamination of the reference reflection plate from the deposition of sample thereupon is prevented, thereby ensuring an accurate measurement of a blank value at all time, but also the improvement in overall measurement accuracy can be accomplished.

What we claim is:

1. A biochemical measuring instrument comprising:
   a reference reflection plate;
   reflection sensor means for obtaining a reflective property of a reflection surface of said reference reflection plate and for obtaining a reflective property of a test paper impregnated with a biochemical sample and mounted on a test stick inserted in said instrument between the reference reflection plate and the reflection sensor means; and
   evaluating means for evaluating a biochemical value of the biochemical sample by comparing the two reflective properties,
   wherein said reflection surface of said reference reflection plate is depressed from the periphery of said reference reflection plate, is substantially flat and is disposed parallel to a direction of insertion of the test stick.

2. A biochemical measuring instrument as defined at a portion of the bottom surface of said reference reflection plate depressed from the periphery.

3. A biochemical measuring instrument as defined in claim 1, further comprising a test stick holder having a window formed therein adapted to hold a test stick inserted therethrough, said window being disposed such that a test paper mounted on the test stick inserted therethrough is held between the reference reflection plate and the reflection sensor means.

* * * * *